United States Patent
Gupta et al.

(10) Patent No.: US 11,026,649 B2
(45) Date of Patent: Jun. 8, 2021

(54) METHOD AND SYSTEM FOR DETERMINING TUMOR BURDEN IN MEDICAL IMAGES

(71) Applicants: Mayank Gupta, Bangalore (IN); Bruce S. Spottiswoode, Knoxville, TN (US)

(72) Inventors: Mayank Gupta, Bangalore (IN); Bruce S. Spottiswoode, Knoxville, TN (US)

(73) Assignee: SIEMENS MEDICAL SOLUTIONS USA, INC., Malvern, PA (US)

(*) Notice: Subject to any disclaimer, the term of this patent is extended or adjusted under 35 U.S.C. 154(b) by 204 days.

(21) Appl. No.: 16/016,998

(22) Filed: Jun. 25, 2018

(65) Prior Publication Data
US 2019/0388049 A1 Dec. 26, 2019

(51) Int. Cl.
*A61B 6/00* (2006.01)
*G06T 7/00* (2017.01)
*G06T 7/11* (2017.01)

(52) U.S. Cl.
CPC .......... *A61B 6/5217* (2013.01); *G06T 7/0012* (2013.01); *A61B 6/461* (2013.01); *A61B 6/485* (2013.01); *A61B 6/5235* (2013.01); *G06T 7/11* (2017.01); *G06T 2207/30096* (2013.01)

(58) Field of Classification Search
CPC ..... A61B 6/5217; A61B 6/485; A61B 6/5233; A61B 6/461; G06T 7/012; G06T 7/11; G06T 2207/30096; G06T 7/0012
See application file for complete search history.

(56) References Cited

U.S. PATENT DOCUMENTS

| | | |
|---|---|---|
| 2011/0142320 A1 | 6/2011 | Gupta |
| 2012/0027273 A1 | 2/2012 | Zankowski |
| 2012/0070052 A1 | 3/2012 | Maroy |
| 2014/0085453 A1* | 3/2014 | Yamane .................. G06T 11/00 348/79 |
| 2017/0046848 A1* | 2/2017 | Jo .......................... G06T 7/0012 |
| 2018/0208647 A1* | 7/2018 | Ferrara .............. A61K 39/3955 |
| 2019/0209116 A1* | 7/2019 | Sjostrand .................. G06T 7/11 |
| 2019/0355117 A1* | 11/2019 | Tan ........................ G06T 7/0012 |

OTHER PUBLICATIONS

Canadian Examiner's Report for Canadian Application No. 3047564 dated Jul. 28, 2020.

* cited by examiner

*Primary Examiner* — Wayne H Cai
(74) *Attorney, Agent, or Firm* — Lempia Summerfield Katz LLC

(57) ABSTRACT

A method and system for determining system-based tumor burden is disclosed. In one aspect, the method includes obtaining the medical image from a source, through an interface. Additionally, the method includes identifying a first region of interest in the medical image. The method also includes selecting from the first region of interest a second region of interest whose tumor burden is to be determined. Furthermore, the method includes defining a segmentation criterion for the second region of interest. The method also includes determining the tumor burden for the second region of interest.

21 Claims, 7 Drawing Sheets

US 11,026,649 B2

METHOD AND SYSTEM FOR DETERMINING TUMOR BURDEN IN MEDICAL IMAGES

FIELD OF TECHNOLOGY

The present disclosure relates to the field of analysis of medical images and more particularly to the field of determining tumor burden in medical images.

BACKGROUND

Tumor burden refers to the number of cancer cells or the amount of cancer tissue in a human body. Tumor burden may be a major prognostic indicator in oncology. Therefore, measures of tumor burden such as metabolic tumor volume (MTV) or total lesion glycolysis (TLG) in anatomical regions relevant for a particular cancer are useful for staging, treatment planning and response assessment. However, such measurements may be labor-intensive and time consuming.

Currently available post processing applications in oncology are capable of automatically segmenting tumor regions or hotspots and estimating tumor burden. Certain post-processing applications known in the prior art enable a physician to manually create a bounding box around a region in a medical image thereby including or excluding clinically relevant/irrelevant regions for further analysis. For example, the Hermes Tumor Finder offers a skeletal segmentation for exclusion of physiological uptake in lymphoma. There may be several limitations to the existing post processing applications for estimating tumor burden. Automatic lesion detection on a positron emission tomography (PET) image works based on a single standardized uptake value threshold for the whole medical image volume. However, some organs may elicit higher/lower physiological uptake than others. For example, the brain, heart, and liver have relatively high uptake of a radiopharmaceutical compound fluorodeoxyglucose (FDG) due to high glucose metabolism. However, the standardized uptake value of FDG in lung may be relatively low. Such variations may introduce either false positives or false negatives when a global threshold is used for lesion detection. Furthermore, current methods of estimating tumor burden rely on manual exclusion of tumor hotspots for regions where there is a physiological uptake. Additionally, these current methods do not support automatic organ/system-based segmentation and organ/system-based tumor burden calculations.

Therefore, there exists a need for a method to determine tumor burden using anatomical classification that is accurate and enables faster medical analysis.

The object of the disclosure is therefore to provide a method and a system to determine tumor burden in a medical image that is accurate, fast and reliable.

SUMMARY

A method and system for determining a tumor burden in a medical image is disclosed. In one aspect, the method includes obtaining the medical image from a source, through an interface. The method also includes identifying a first region of interest in the medical image. The method further includes selecting from the first region of interest a second region of interest in which tumor burdens are to be determined. Additionally, the method includes defining a segmentation criteria for the second region of interest. Furthermore, the method includes determining the tumor burden for the second region of interest.

In another aspect, a system for determining total tumor burden in a medical image includes a processing unit; a medical database coupled to the processing unit and a memory coupled to the processing unit. The memory includes a tumor burden estimation module configured for obtaining the medical image from a source, through an interface. The tumor burden estimation module is further configured to identify a first region of interest in the medical image. Additionally, the tumor burden estimation module is configured to select from the first region of interest a second region of interest whose tumor burden is to be determined. The tumor burden estimation module is further configured to define a segmentation criterion for the second region of interest. Furthermore, the tumor burden estimation module is configured to determining the tumor burden for the second region of interest.

In yet another aspect, a non-transitory computer-readable storage medium having machine-readable instructions stored therein, that when executed by the server, causes the server to perform the method acts as described above.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present disclosure is further described hereinafter with reference to illustrated embodiments shown in the accompanying drawings, in which.

DETAILED DESCRIPTION

Figure 1:
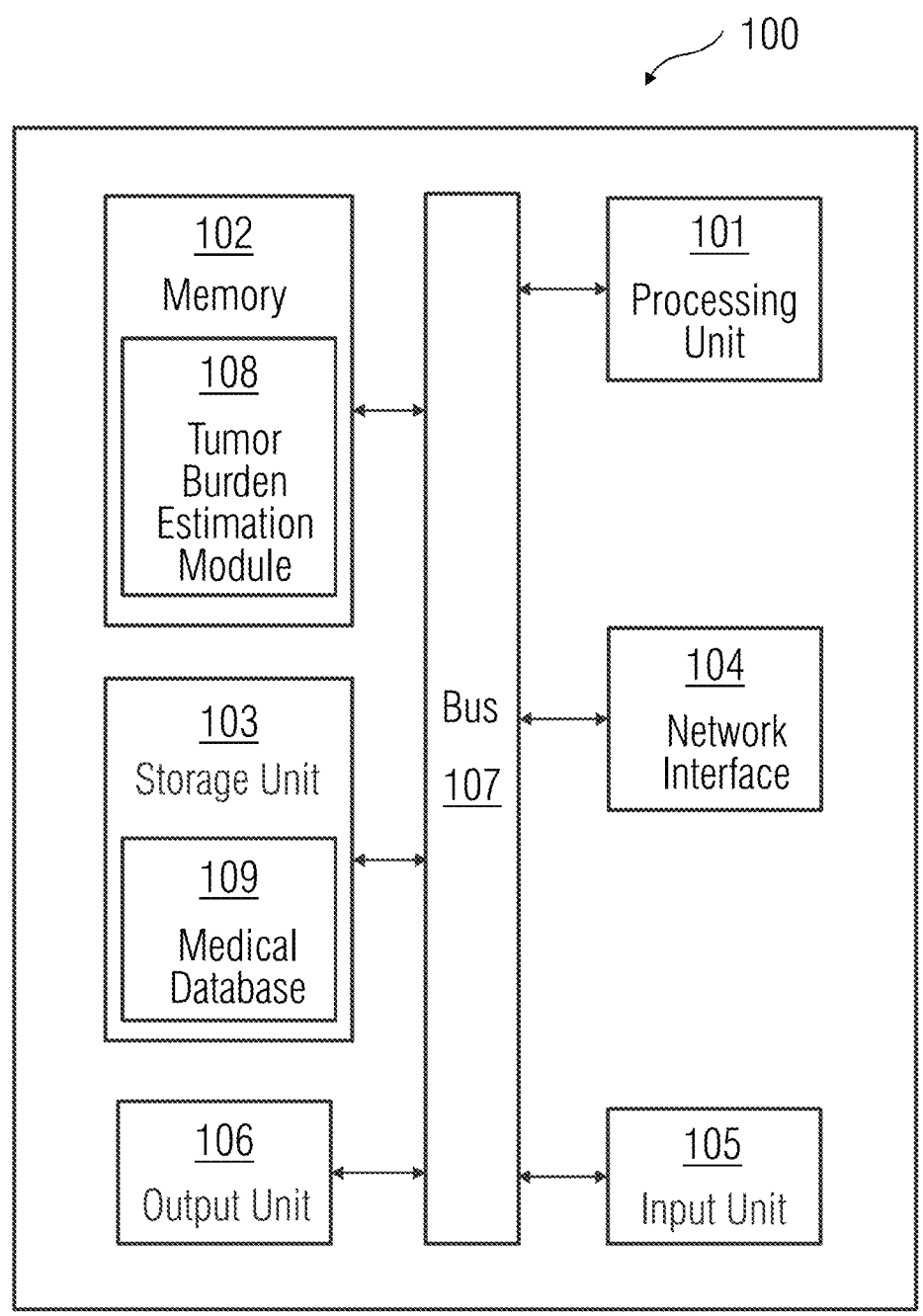
FIG. 1 illustrates a block diagram of a system in which an embodiment of a method for determining tumor burden in a medical image may be implemented.

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

FIG. 1 is a block diagram of a system 100 in which an embodiment may be implemented, for example, as a system to determine a tumor burden in a medical image, configured to perform the processes as described therein. In FIG. 1, the system 100 includes a processing unit 101, a memory 102, a storage unit 103, a network interface 104, an input unit 105, an output unit 106 and a standard interface or bus 107. The system 100 may be a (personal) computer, a workstation, a virtual machine running on host hardware, a microcontroller, or an integrated circuit. As an alternative, the system 100 may be a real or a virtual group of computers (the technical term for a real group of computers is "cluster", the technical term for a virtual group of computers is "cloud").

The processing unit 101, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 101 may also include embedded controllers, such as generic or programmable logic devices or arrays, application specific integrated circuits, single-chip computers, and the like. In general, a processing unit 101 may include hardware elements and software elements. The processing unit 101 may be configured for multithreading, e.g., the processing unit 101 may host different calculation processes at the same time, executing the either in parallel or switching between active and passive calculation processes.

The memory 102 may be volatile memory and non-volatile memory. The memory 102 may be coupled for communication with the processing unit 101. The processing unit 101 may execute instructions and/or code stored in the memory 102. A variety of computer-readable storage media may be stored in and accessed from the memory 102. The memory 102 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 102 includes a tumor burden estimation module 108 stored in the form of machine-readable instructions on any of the above-mentioned storage media and may be in communication to and executed by processing unit 101. When executed by the processing unit 101, the tumor burden estimation module 108 causes the processing unit 101 to determine a tumor load or tumor burden in the medical image. Method acts executed by the processing unit 101 to achieve the abovementioned functionality are elaborated upon in detail in FIGS. 2, 3, 4, 5, and 6.

The storage unit 103 may be a non-transitory storage medium which stores a medical database 109. The medical database 109 is a repository of medical information related to one or more patients that is maintained by a healthcare service provider. The input unit 105 may include an input device such as keypad, touch-sensitive display, camera (such as a camera receiving gesture-based inputs), etc. capable of receiving input signal. The bus 107 acts as interconnect between the processing unit 101, the memory 102, the storage unit 103, the network interface 104, the input unit 105 and the output unit 106.

Those of ordinary skilled in the art will appreciate that the hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter also may be used in addition or in place of the hardware depicted. The depicted example is provided for the purpose of explanation only and is not meant to imply architectural limitations with respect to the present disclosure.

A system in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Wash. may be employed if suitably modified. The operating system is modified or created in accordance with the present disclosure as described.

Disclosed embodiments provide systems and methods for analysing a medical image. In particular, the systems and methods may determine a tumor load in a medical image.

Figure 2:
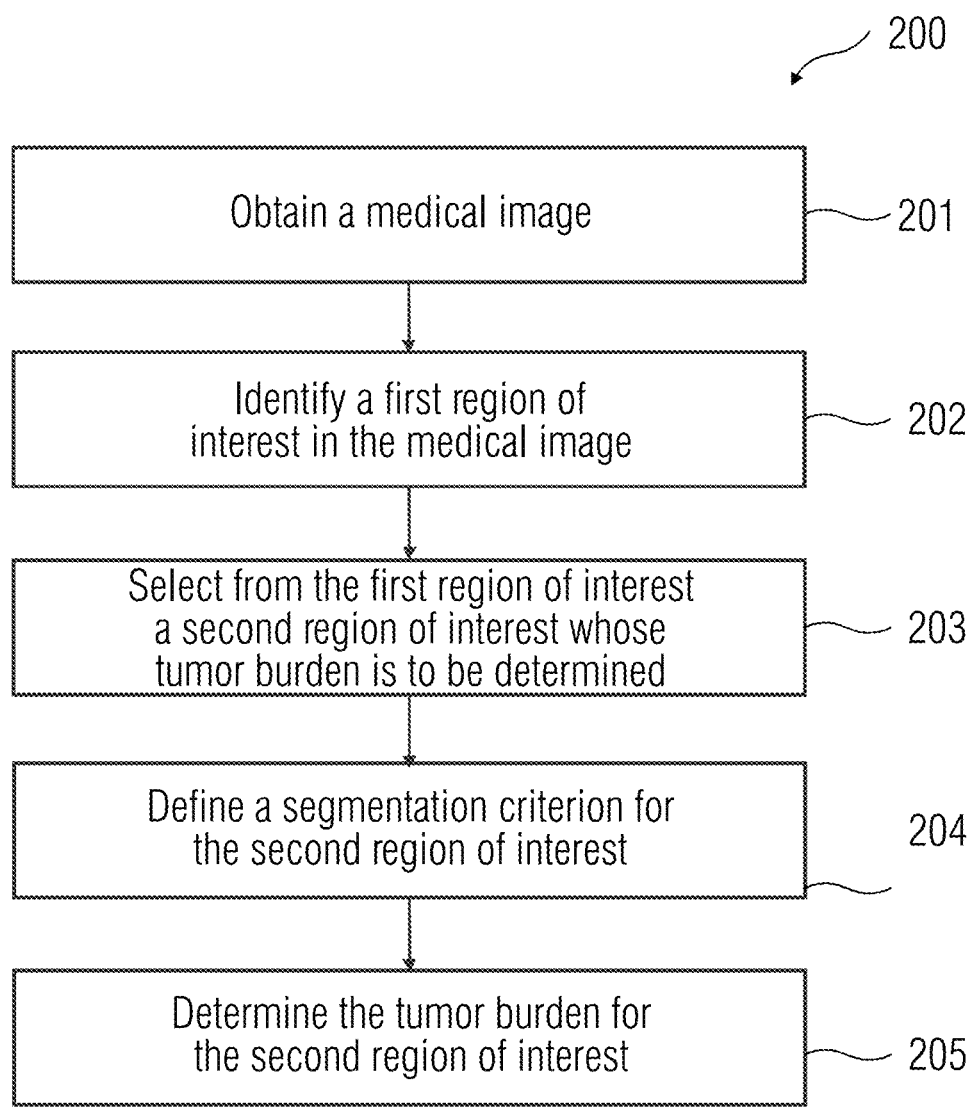
FIG. 2 illustrates a flowchart of an embodiment of a method of determining tumor burden in a medical image.

FIG. 2 illustrates a flowchart of an embodiment of a method 200 of determining a tumor burden in a medical image. At act 201 of the method 200, a medical image is obtained from a source. The source may be, for example, a medical imaging device such as a positron emission tomography (PET) device. Alternatively, the medical image may also be obtained from the medical database 109. The medical image may be obtained from the source through an interface. The interface may be, for example, the network interface 105 or standard interface 107. The medical image may be, for example, a positron emission tomography image. Alternatively, depending on the type of medical imaging modality used, the medical image may be, for example, a computed tomography image or a magnetic resonance imaging image or a combination of different types of medical images obtained from one or more imaging modalities. The medical image may include imaging information pertaining to one or more organs or structures in the patient's body. Such imaging information may include, for example, segmentation volumes of organs such as, but not limited to, brain, heart, liver, lungs, kidney, bladder, and prostrate. The imaging information may also include, for example, two-dimensional or three-dimensional ranges or bounding boxes associated with head and neck, thorax, abdomen, pelvis, lower limbs, and lymph node stations. The imaging information may further include, for example, bones such as cortical bone, trabecular bone and marrow.

At act 202, a first region of interest is identified in the medical image. The first region of interest may include a combination of one or more organs and/or one or more anatomical ranges. The first region of interest may be defined by a physician and may be based on the physical volume of the patient's body that may require medical analysis. The first region of interest may further be identified based on the one or more organs or anatomical ranges or combinations of both that are to be analysed. Therefore, for example, if the physician intends to determine tumor burden of liver of the patient, the first region of interest identified may be the abdominal range. At act 203, a second region of interest whose tumor burden is to be determined is selected from the first region of interest. In an embodiment, the second region of interest may include at least one organ or anatomical range or a combination thereof, from the first region of interest. The second region of interest may be defined based on the anatomical, physiological, and/or pathophysiological relationship between one or more organs and or anatomical ranges. Such relationship may differ based on the radiopharmaceutical compound used in the image acquisition process. Such relationship may be determined based on cancer staging and may therefore depend on the organs or anatomical ranges that may have been affected due to disease progression. In an embodiment, the second region of interest may therefore be pre-defined based on the type and stage of a cancer. The physician may specify the second region of interest to be selected from the first region of interest for determination of tumor burden. The physician may access such information related to the one or more organs present in the first region of interest via a graphical user interface. The graphical user interface may be used by the physician to indicate at least one organ within the first region of interest whose tumor burden is to be determined. The graphical user interface may include information associated with one or more organs in the first region of interest that may be chosen by the physician for tumor burden determination. The physician may select one or more data fields, for example, by clicking a mouse button on the option. In an alternate embodiment, the second region of interest may be selected by excluding one or more organs and/or anatomical ranges from the first region of interest. For example, the physician may choose from the graphical user interface the organs or anatomical ranges to be excluded from the first region of interest for tumor burden determination. In one embodiment, the click of the mouse button may proceed in checking or unchecking the data fields associated with the one or more organs in the first region of interest on the graphical user interface.

Figure 3:
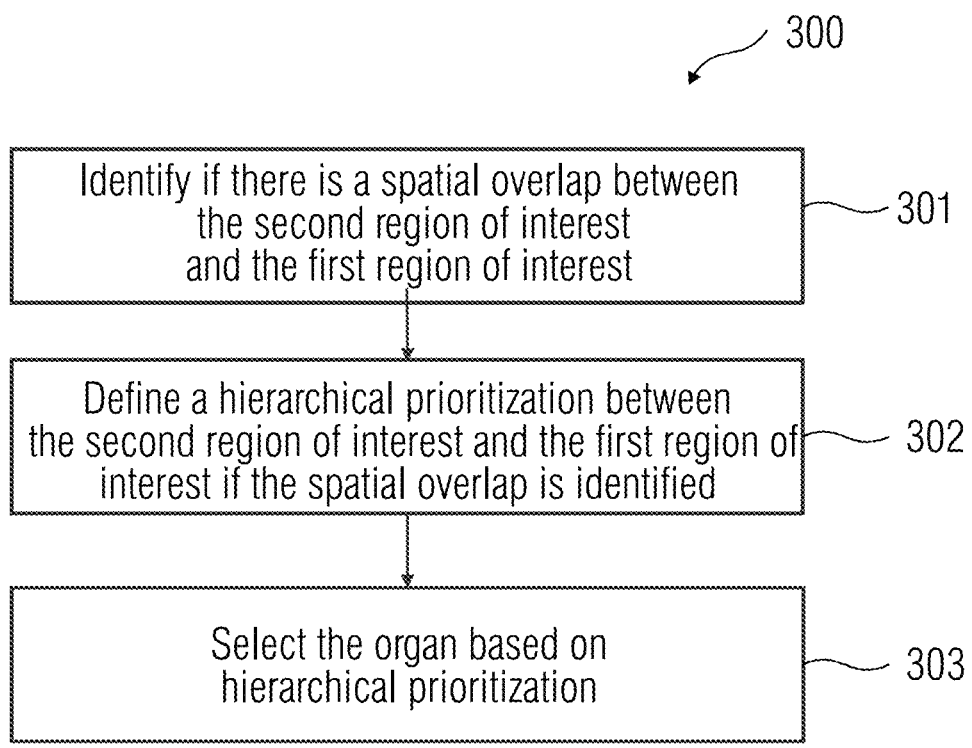
FIG. 3 illustrates a flowchart of an embodiment of a method of selecting the second region of interest whose tumor burden is to be determined.
Figure 4:
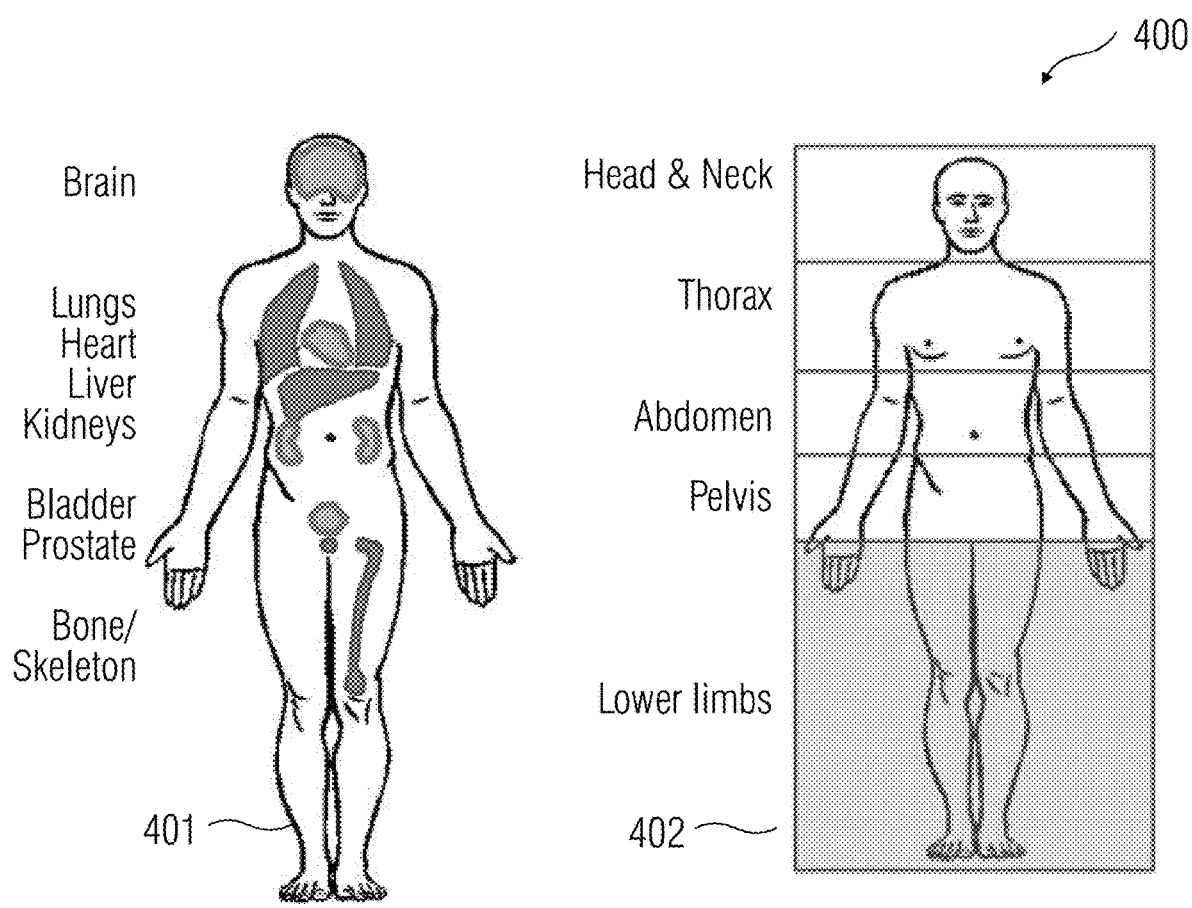
FIG. 4 illustrates an embodiment of a configuration of deriving tumor burden in a defined region in a human body.

FIG. 3 illustrates a flowchart of an embodiment of a method 300 of selecting the second region of interest from the first region of interest, whose tumor burden is to be determined. At act 301, presence of a spatial overlap between the second region of interest and the first region of interest is identified. A spatial overlap may occur when two or more organs are present or enclosed in the same anatomical region. Such spatial overlap may result in an inaccurate determination of tumor burden. Therefore, at act 302, a hierarchical priority is defined between the second region of interest and the spatially overlapping first region of interest. In an embodiment, the spatial hierarchy may be defined such that an organ takes priority over an anatomical range. At act 303, the second region of interest is selected based on the defined hierarchical priority. Advantageously, defining a hierarchical priority eliminates the chances of duplicate segmentations. Therefore, in an example of overlapping liver organ and abdominal region, the hierarchical prioritization for selection may be defined as:

a. Case 1: Include abdomen and exclude liver
  i. For liver region: do nothing ii. For abdominal region:
    1. Segmentation volume: abdomen volume excluding liver volume
    2. Segmentation criteria: abdomen segmentation criteria
b. Case 2: Exclude abdomen and include liver
  i. For liver region:
    1. Segmentation volume: liver volume
    2. Segmentation criteria: liver segmentation criteria
  ii. For abdominal region: do nothing.
c. Case 3: Include abdomen and include liver
  i. For liver region:
    1. Segmentation volume: liver volume
    2. Segmentation criteria: liver segmentation criteria
  ii. For abdominal region:
    1. Segmentation volume: abdomen volume excluding liver volume
    2. Segmentation criteria: abdomen segmentation criteria FIG. 4 illustrates an embodiment of a configuration 400 of determining a tumor burden in a whole body, excluding physiological uptake in the regions of brain, heart, kidneys, bladder and lower limbs. The first anatomy 401 illustrates a plurality of segmented organs that are present in different regions in the patient's body. The second anatomy 402 illustrates one or more anatomical ranges that enable the physician to choose a region of interest. In an embodiment, as illustrated in FIG. 4, the first region of interest identified is the whole body of the patient. The second region of interest, therefore, may include regions and/or organs excluding brain, heart, kidneys, bladder and lower limbs. Therefore, according to FIG. 4, the second region of interest includes lungs, liver, and bone/skeleton. The organs in the second region of interest are indicated in light grey.

Figure 5:
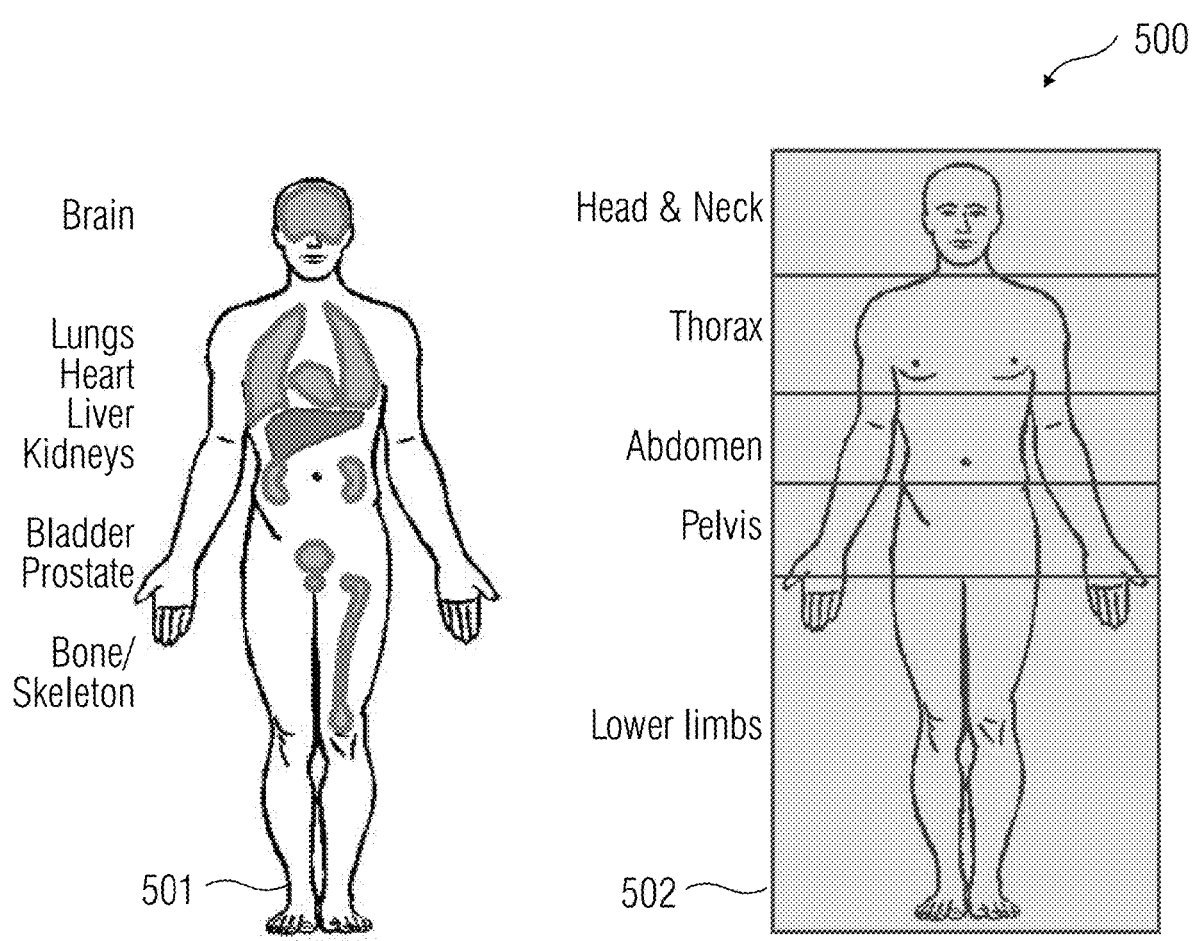
FIG. 5 illustrates another embodiment of a configuration of deriving tumor burden in a defined region in a human body.

Similarly, FIG. 5 illustrates an embodiment of a configuration 500 of deriving organ-specific tumor burden for liver. The anatomy 502 indicates the anatomical ranges in the patient's body. In the embodiment, the second region of interest, e.g., liver is selected for further analysis. The anatomy 501 depicts a plurality of organs included in the whole body of the patient. However, as the liver is selected or included as the second region of interest, the liver is represented in light grey. Therefore, all the other organs are excluded from the second region of interest and therefore represented in dark grey.

Figure 6:
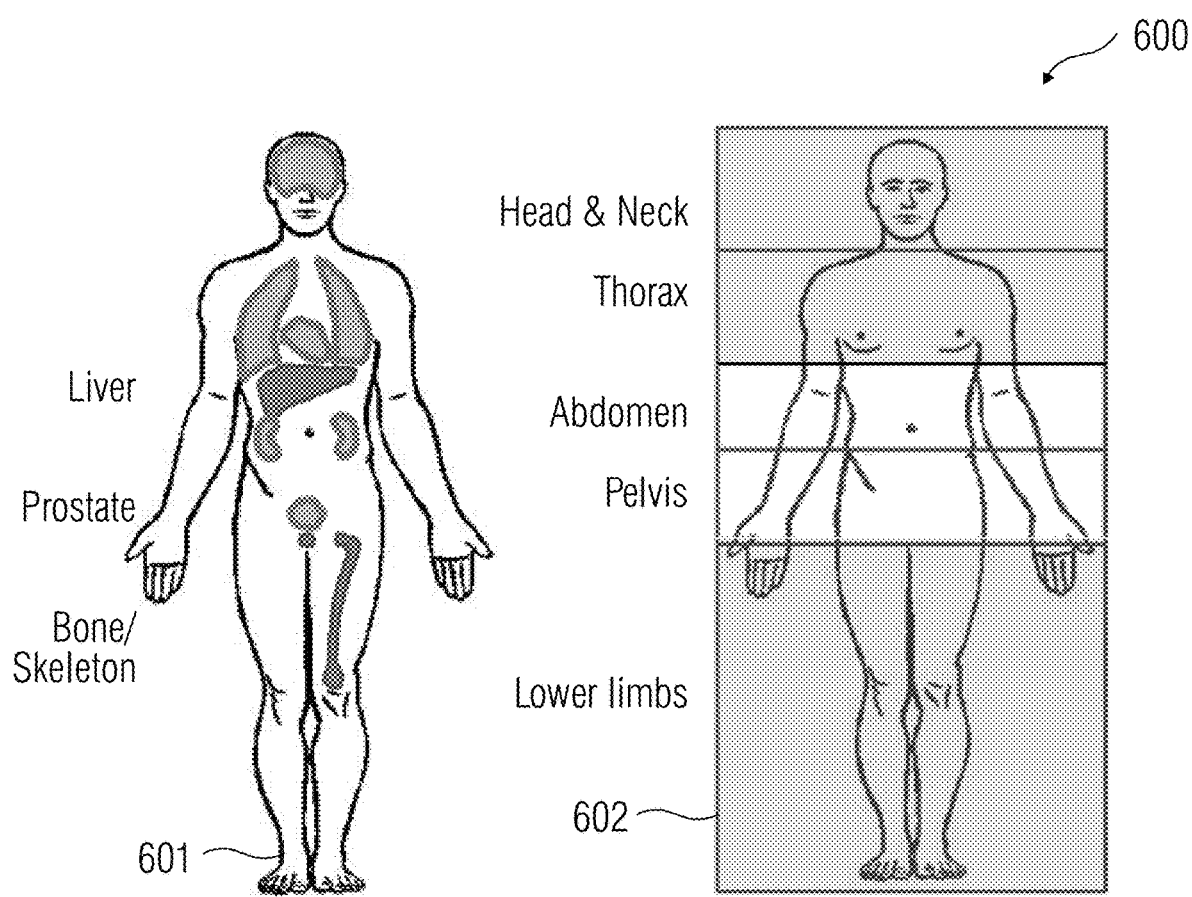
FIG. 6 illustrates yet another embodiment of a configuration of deriving tumor burden in a defined region in a human body.

In yet another example, FIG. 6 illustrates a configuration 600 of deriving tumor burden in the pathophysiological system for prostate cancer, providing pelvic, abdominal and skeletal tumour burden whilst excluding physiological PET uptake. The pathophysiological system for prostate cancer may include the prostate gland, the liver and the bone or skeletal system of the patient. The anatomy 602 illustrates the anatomical range chosen as the first region of interest and the anatomy 601 illustrates a plurality of organs selected in the first region of interest. The anatomy 602 includes pelvis and abdomen regions as the first regions of interest as the pathophysiological system for prostate cancer include organs or anatomical regions present in additional anatomical ranges apart from the pelvis range. The anatomy 601, therefore, depicts the second region of interest forming a part of the pathophysiological system for prostate cancer, e.g., prostate, liver, and bone/skeleton are included and are indicated in light grey. All the other organs are excluded and are therefore represented in dark grey.

At act 204 of the method 200, a segmentation criterion is defined for the second region of interest. The segmentation criterion enables efficient segmentation of the second region of interest for further analysis. Therefore, in an embodiment, if only one organ or an anatomical range is to be analysed in the second region of interest, the segmentation criterion may be defined based on such organ or anatomical range. The segmentation criterion may include at least one segmentation algorithm associated with the one or more organs to be analysed. Such segmentation algorithms may be used to segment the one or more organs and or anatomical regions from the region of interest. Such segmentation algorithms may be well-known to a person skilled in the art.

Figure 7:
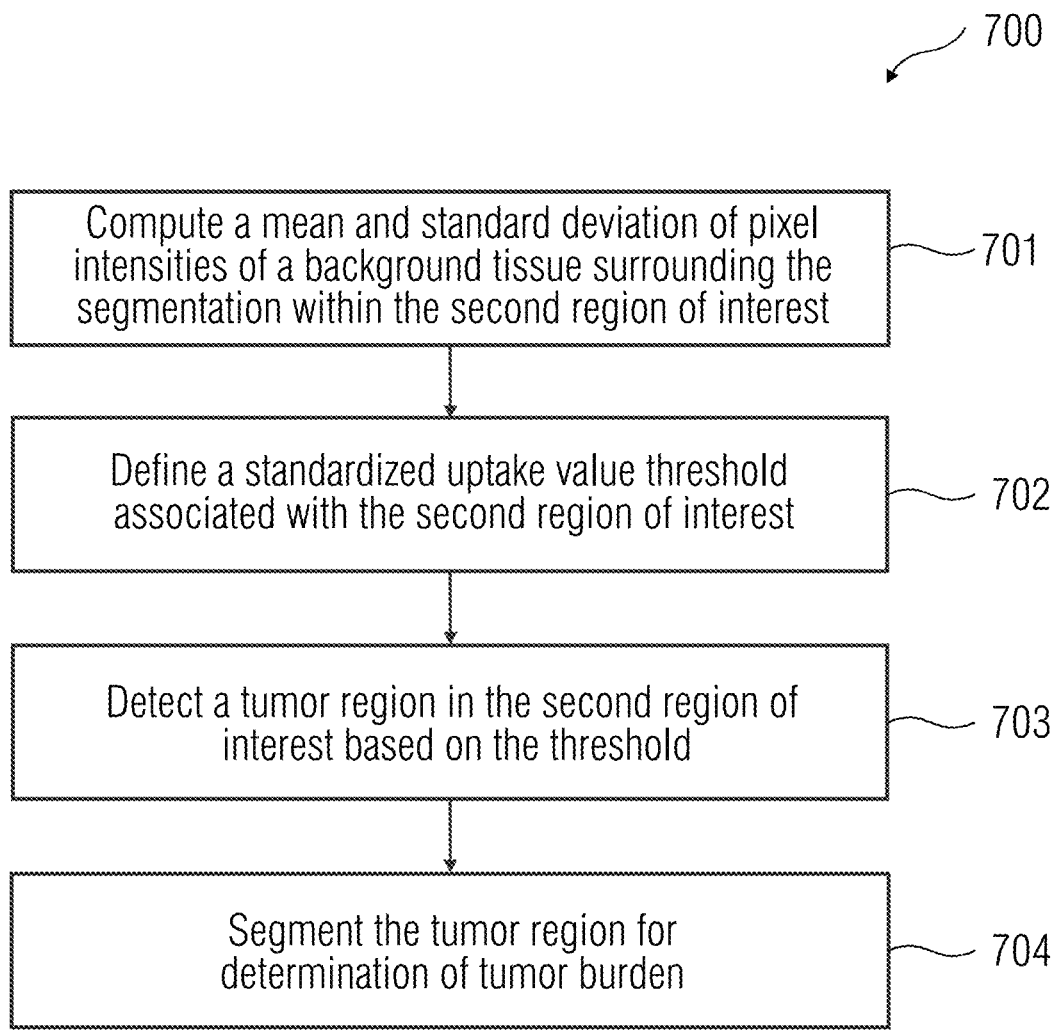
FIG. 7 illustrates a flowchart of an embodiment of a method of defining a segmentation criterion for the second region of interest.

FIG. 7 illustrates a flowchart of an embodiment of a method 700 of defining a segmentation criterion for the second region of interest. At act 701 of the method 700, a mean and a standard deviation value is computed for pixel intensities in a background tissue surrounding the segmentation within the second region of interest. In an embodiment, the standardized uptake value threshold may be defined based on pixel intensities of background tissue surrounding segmentation(s) within the second region of interest. Such tissue may be a part of the first region of interest. In defining the standardized uptake value threshold, a mean and standard deviation value of pixel intensities of the background tissue is calculated. Such background tissue may be a non-cancerous tissue. Therefore, at act 702, based on the pixel intensity of the background tissue of the second region of interest, the standardized uptake value threshold may be adaptively defined. Such standardized uptake value threshold may be associated with the selected organ or the anatomical range in the second region of interest whose tumor burden is to be determined. Therefore, the segmentation criterion may be adaptively defined based on the background uptake region of the second region of interest. A standardized uptake value is a ratio of the image derived radioactivity concentration and the whole body concentration of the injected radioactivity. Each organ or anatomical range may have an associated standardized uptake value threshold. Such thresholds therefore vary from one organ/anatomical range to another. The standardized uptake value threshold enables detection of lesions in the patient's body. Therefore, based on the selected organ/anatomical region the standardized uptake value threshold is defined such that lesions may be detected accurately in the patient's body. For example, if radiopharmaceutical compound used in the imaging process is fluorodeoxyglucose (FDG), a low standard uptake value threshold may be set for lungs as the uptake of FDG is low for lungs. Similarly, a higher threshold may be set for liver as the uptake of fluorodeoxyglucose in liver is high. Therefore, origin of false positives and false negatives in the lesion detection process may be eliminated. At act 703 of the method 700, a tumor region is detected automatically in the second region of interest based on the standardized tumor uptake value threshold. Such automatic tumor detection may be performed, for example, using inverted grayscale look-up table. Alternatively, other methods well known to a person skilled in the art may be used for automated tumor detection in the selected organ. At act 704, the tumor region may be segmented from the second region of interest for determination of tumor burden. The tumor burden for the segmented tumor region may then be determined at act 205 of the method 200.

In an embodiment, the foregoing method acts may be used to evaluate specific types of cancer based on cancer staging criteria. A plurality of configuration of organs and/or anatomical ranges may be pre-defined based on the type of cancer to be evaluated. Such configurations may be defined based on the organ system to be considered for cancer analysis and a knowledge of the organs or anatomical ranges that may be affected. For example, a configuration relevant for prostate cancer may include anatomical regions such as prostate (for a confined relapse); pelvic region (for local lymph nodes); abdominal region (for distant lymph node and visceral organ metastases); and skeleton (for bone metastases). Each of these anatomical regions may be indicative of a different treatment pathway. According to another example, a configuration relevant for breast cancer may include anatomical regions such as breast (for primary tumors); contralateral breast and axillary, mammary and supraclavicular lymph nodes (for regional spread); lungs, liver, and brain (for visceral or distant metastases); and skeleton (for bone metastases). Yet another configuration may be for, for example, lung cancer. Such configuration may include anatomical regions such as lung (for primary tumor); contralateral lung and mediastinal, supraclavicular, and hilar lymph nodes (for regional spread); liver, brain and adrenal glands (for visceral or distant metastases) and skeleton (for bone metastases). Therefore, in an embodiment, a plurality of tumor regions may be determined based on the standardized uptake value threshold for the pre-defined configuration. This enables determination of system-based tumor burden for the patient.

In an embodiment, the pre-defined configurations for the system-based tumor burden determination may be stored in the medical database 109 and may be provided as an option on the graphical user interface. In another embodiment, the physician may create a new configuration for tumor burden analysis, including a plurality of organs and/or anatomical ranges, based on his expertise. Such new configurations may also be stored in the medical database 109 for future use and analysis. The tumor burden estimation module 108 may be configured to determine tumor burden in the corresponding second region of interest of each of such stored configurations, every time such stored configuration is chosen by the physician.

In another embodiment, a temporal trend of the configuration based tumor burden assessment may be represented for example, graphically as a trend graph. Such trend graphs may provide inputs on the progression of the disease in the region(s) of interest. Therefore, clinical decision making process is enhanced and made efficient.

The foregoing examples have been provided merely for the purpose of explanation and are in no way to be construed as limiting of the present disclosure. While the disclosure has been described with reference to various embodiments, it is understood that the words, which have been used herein, are words of description and illustration, rather than words of limitation. Further, although the disclosure has been described herein with reference to particular means, materials, and embodiments, the disclosure is not intended to be limited to the particulars disclosed herein; rather, the disclosure extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosure in its aspects.

What is claimed is:

1. A method of determining a system-based tumor burden in a medical image, the method comprising:
   obtaining the medical image from a source through an interface;
   identifying a first region of interest in the medical image, wherein the first region of interest comprises one or more anatomical ranges of a body of a patient, the one or more anatomical ranges comprising a head and neck, a thorax, an abdomen, a pelvis, lower limbs of the patient, or a combination thereof;

selecting from the first region of interest a second region of interest whose tumor burden is to be determined, wherein the second region of interest comprises at least one organ, at least one anatomical range, or a combination thereof from the first region of interest, and wherein the second region of interest is defined based on a physiological relationship and/or a pathophysiological relationship between organs, between anatomical ranges, between at least one organ and at least one anatomical range, or a combination thereof, defining a segmentation criterion for the second region of interest; and determining the tumor burden for the second region of interest.

2. The method of claim 1, wherein, in the defining of the segmentation criterion, the method comprises:

defining a standardized uptake value threshold associated with the second region of interest;

detecting a tumor region within the second region of interest based on the standardized uptake value threshold; and segmenting the tumor region from the second region of interest.

3. The method of claim 2, wherein the standardized uptake value threshold of the second region of interest is defined based on a pixel intensity of a tissue surrounding segmentation within the second region of interest, wherein the tissue is a part of the first region of interest.

4. The method of claim 1, wherein the selecting of the second region of interest further comprises:

identifying a spatial overlap between the second region of interest and the first region of interest; and defining a hierarchical prioritization between the second region of interest and the first region of interest when the spatial overlap is identified.

5. The method of claim 4, wherein, in the defining of the hierarchical prioritization, an organ takes priority over an anatomical range.

6. The method of claim 1, further comprising:

generating a temporal trend of the tumor burden for the second region of interest determined over a defined interval of time.

7. The method of claim 1, wherein the first and the second regions of interest are defined using one or more of a computed tomography image, a magnetic resonance imaging image, and a positron emission tomography image.

8. The method of claim 1, wherein the second region of interest is stored as an organ system configuration.

9. The method of claim 1, wherein the physiological relationship or the pathophysiological relationship differs based on a radiopharmaceutical compound used in an acquisition of the medical image.

10. The method of claim 1, wherein the second region of interest is pre-defined based on a type of cancer and/or a stage of the cancer in the body of the patient.

11. A system for determining a total tumor burden in a medical image, the system comprising:

a processing unit;

a medical database coupled to the processing unit;

a memory coupled to the processing unit, wherein the memory and processing unit are configured to:

obtain the medical image from a source, through an interface;

identify a first region of interest in the medical image, wherein the first region of interest comprises one or more anatomical ranges of a body of a patient, the one or more anatomical ranges comprising a head and neck, a thorax, an abdomen, a pelvis, lower limbs of the patient, or a combination thereof;

select from the first region of interest a second region of interest whose tumor burden is to be determined, wherein the second region of interest comprises at least one organ, at least one anatomical range, or a combination thereof from the first region of interest, and wherein the second region of interest is defined based on a physiological relationship and/or a pathophysiological relationship between organs, between anatomical ranges, between at least one organ and at least one anatomical range, or a combination thereof;

define a segmentation criterion for the second region of interest; and determine the tumor burden for the second region of interest.

12. The system of claim 11, wherein, in the defining of the segmentation criterion, the memory and the processing unit are further configured to:

define a standardized uptake value threshold associated with the second region of interest;

detect a tumor region within the second region of interest; and determine the tumor burden for the second region of interest based on the standardized uptake value threshold.

13. The system of claim 12, wherein the memory and the processing unit are further configured to define the standardized uptake value threshold of the second region of interest based on a pixel intensity of a tissue surrounding segmentation within the second region of interest, wherein the tissue is a part of the first region of interest.

14. The system of claim 11, wherein, in the selection of the second region of interest, the memory and the processing unit are further configured to define a hierarchical prioritization where there is a spatial overlap between the second region of interest and the first region of interest.

15. The system of claim 11, wherein the memory and the processing unit are further configured to generate a temporal trend of the tumor burden for the second region of interest determined over defined intervals of time.

16. The system of claim 11, wherein the memory and the processing unit are further configured to define the first region of interest and the second region of interest using one or more of a computed tomography image, a magnetic resonance imaging image, and a positron emission tomography image.

17. A non-transitory computer-readable storage medium having machine-readable instructions stored therein, that when executed by a server, cause the server to:

obtain a medical image from a source through an interface;

identify a first region of interest in the medical image, wherein the first region of interest comprises one or more anatomical ranges of a body of a patient, the one or more anatomical ranges comprising a head and neck, a thorax, an abdomen, a pelvis, lower limbs of the patient, or a combination thereof;

select from the first region of interest a second region of interest whose tumor burden is to be determined, wherein the second region of interest comprises at least one organ, at least one anatomical range, or a combination thereof from the first region of interest, and wherein the second region of interest is defined based on a physiological relationship and/or a pathophysiological relationship between organs, between anatomical ranges, between at least one organ and at least one anatomical range, or a combination thereof;

define a segmentation criterion for the second region of interest; and determine the tumor burden for the second region of interest.

18. The storage medium of claim 17, wherein the instructions further cause the server to:

define a standardized uptake value threshold associated with the second region of interest;

detect a tumor region within the second region of interest; and determine the tumor burden for the second region of interest based on the standardized uptake value threshold.

19. The storage medium of claim 18, wherein the instructions cause the server to:

define the standardized uptake value threshold of the second region of interest based on a pixel intensity of a tissue surrounding segmentation within the second region of interest, wherein the tissue is a part of the first region of interest.

20. The storage medium of claim 17, wherein, in the selection of the second region of interest, the instructions cause the server to define a hierarchical prioritization between where there is a spatial overlap between the second region of interest and the first region of interest.

21. The storage medium of claim 17, wherein the instructions cause the server to:

define the first region of interest and the second region of interest using one or more of a computed tomography image, a magnetic resonance imaging image, and a positron emission tomography image.

* * * * *